(12) United States Patent
Chen et al.

(10) Patent No.: US 6,837,708 B2
(45) Date of Patent: Jan. 4, 2005

(54) DEVICE FOR GENERATING A JET STREAM OF AIR ENTRAINED WATER

(76) Inventors: Chien-Liang Chen, 7F, No. 136, Sec. 2, Ho-Ping W. Rd., Taipei City (TW); Chien-Chuan Chen, 7F, No. 136, Sec. 2, Ho-Ping W. Rd., Taipei City (TW); I-Chun Chen, 7F, No. 136, Sec. 2, Ho-Ping W. Rd., Taipei City (TW)

( * ) Notice: Subject to any disclaimer, the term of this patent is extended or adjusted under 35 U.S.C. 154(b) by 460 days.

(21) Appl. No.: 10/133,577

(22) Filed: Apr. 29, 2002

(65) Prior Publication Data

US 2003/0204154 A1 Oct. 30, 2003

(51) Int. Cl.[7] .............................. A61C 17/02; A61C 1/02
(52) U.S. Cl. .......................................... 433/80; 433/98
(58) Field of Search ............................ 433/80, 84, 98; 222/142, 135, 145.5, 145.4; 239/380, 413, 407

(56) References Cited

U.S. PATENT DOCUMENTS

| | | | | |
|---|---|---|---|---|
| 4,944,676 A | * | 7/1990 | Hu | 433/98 |
| 5,074,787 A | * | 12/1991 | Tsukada | 433/98 |
| 5,201,899 A | * | 4/1993 | Austin et al. | 433/98 |
| 5,556,007 A | * | 9/1996 | Breitsprecher | 222/136 |
| 6,179,614 B1 | * | 1/2001 | Elrod et al. | 433/88 |
| 6,612,465 B2 | * | 9/2003 | Pierson et al. | 222/82 |
| 2003/0077552 A1 | * | 4/2003 | Decosterd et al. | 433/84 |

* cited by examiner

*Primary Examiner*—Cary E. O'Connor
(74) *Attorney, Agent, or Firm*—Patton Boggs LLP

(57) ABSTRACT

A device for generating a jet stream of air entrained water for cleaning teeth and gums, includes two pumps disposed to respectively and sequentially pump in and out of internal ports thereof from first water and air transit chambers, water flow and air stream to generate raised water and air pressures. Two valves are disposed respectively to be moved by the water and air pressures to block or permit entry of the water flow and the air stream into second water and air transit chambers. A mixing outlet is disposed downstream of and to merge water and air outlet ports of the second water and air transit chambers to obtain an accelerated stream of the air entrained water for cleaning teeth and gums.

9 Claims, 5 Drawing Sheets

DEVICE FOR GENERATING A JET STREAM OF AIR ENTRAINED WATER

BACKGROUND OF THE INVENTION

1. Field of the Invention

This invention relates to a device for cleaning teeth and gums, more particularly to a device for generating a jet stream of air entrained water adapted for cleaning teeth and gums.

2. Description of the Related Art

A conventional method for intruding air into water flow in a teeth cleaning apparatus is accelerating the water flow speed so as to generating a jet stream of air entrained water to result in an improved a cleaning effect. However, the increased water pressure, which arises as a result of acceleration of the water flow, will impact the teeth and gums of the user and results in uncomfortable feeling for the user.

SUMMARY OF THE INVENTION

The object of the present invention is to provide a device which can generate a smooth and steady jet stream of air entrained water for cleaning teeth and gums of a user with minimal user discomfort.

According to this invention, the device includes a water inlet for receiving a water flow from a reservoir, an air inlet admitting entrance of air stream, and a water and air mixing body which defines first water and air transit chambers spaced apart from each other, and second water and air transit chambers spaced apart from each other. The first water and air transit chambers respectively have first water and air inlet ports which are communicated respectively with the water inlet and the air inlet, and first water and air outlet ports which are disposed respectively downstream of the first water and air inlet ports. The second water and air transit chambers respectively have second water and air inlet ports which are communicated respectively with the first water and air outlet ports, and second water and air outlet ports which are disposed respectively downstream of the second water and air inlet ports. First and second pumps respectively have first and second internal ports which are communicated respectively with the first water and air transit chambers, and which are disposed respectively downstream of the first water and air inlet ports and upstream of the first water and air outlet ports. The first and second pumps can sequentially pump in and out of the first and second internal ports respectively, the water flow and the air stream respectively, thereby accelerating the speeds of the water flow and the air stream respectively so as to generate raised water and air pressures, respectively.

First and second valves are disposed respectively between the first water inlet port and the first internal port, and between the first air inlet port and the second internal port. Each of the first and second valves is movable between a first closed position, where a respective one of the water flow and the air stream, being pumped out of a respective one of the first and second internal ports, is blocked from passing through a respective one of the first water and air inlet ports, while proceeding further to flow through a respective one of the first water and air outlet ports, and a first open position, where the respective one of the water flow and the air stream is pumped in a respective one of the first water and air transit chambers as well as the respective one of the first and second internal ports through the respective one of the first water and air inlet ports.

Third and fourth valves are disposed respectively between the second water inlet port and the second water outlet port, and between the second air inlet port and the second air outlet port. Each of the third and fourth valves is moved by the respective one of the raised water and air pressures from a second closed position, where the respective one of the water flow and the air stream, which is being pumped in the respective one of the first water and air transit chambers when the respective one of the first and second valves is in the first open position, is blocked from entering into a respective one of the second water and air outlet ports, to a second open position, where the respective one of the water flow and the air stream, which is flowing through the respective one of the first water and air outlet ports when the respective one of the first and second valves is in the first closed position, further proceeds to the respective one of the second water and air outlet ports through a respective one of the second water and air transit chambers. A mixing outlet is disposed downstream of and is disposed to merge the second water and air outlet ports so as to obtain an accelerated stream of the air entrained water.

BRIEF DESCRIPTION OF THE DRAWINGS

Other features and advantages of the present invention will become apparent in the following detailed description of the preferred embodiment of the invention, with reference to the accompanying drawings, in which.

DETAILED DESCRIPTION OF THE PREFERRED EMBODIMENT

Figure 1:
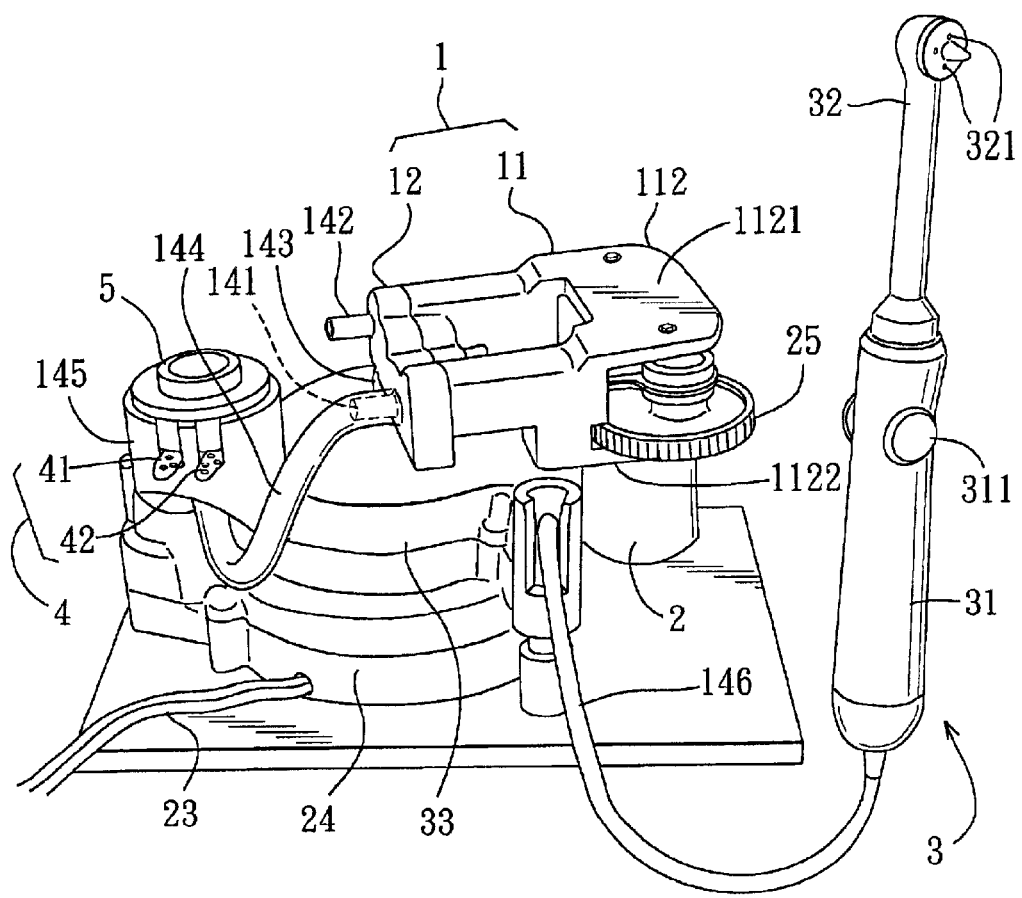
FIG. 1 is a perspective view of a preferred embodiment of a device according to this invention.
Figure 2:
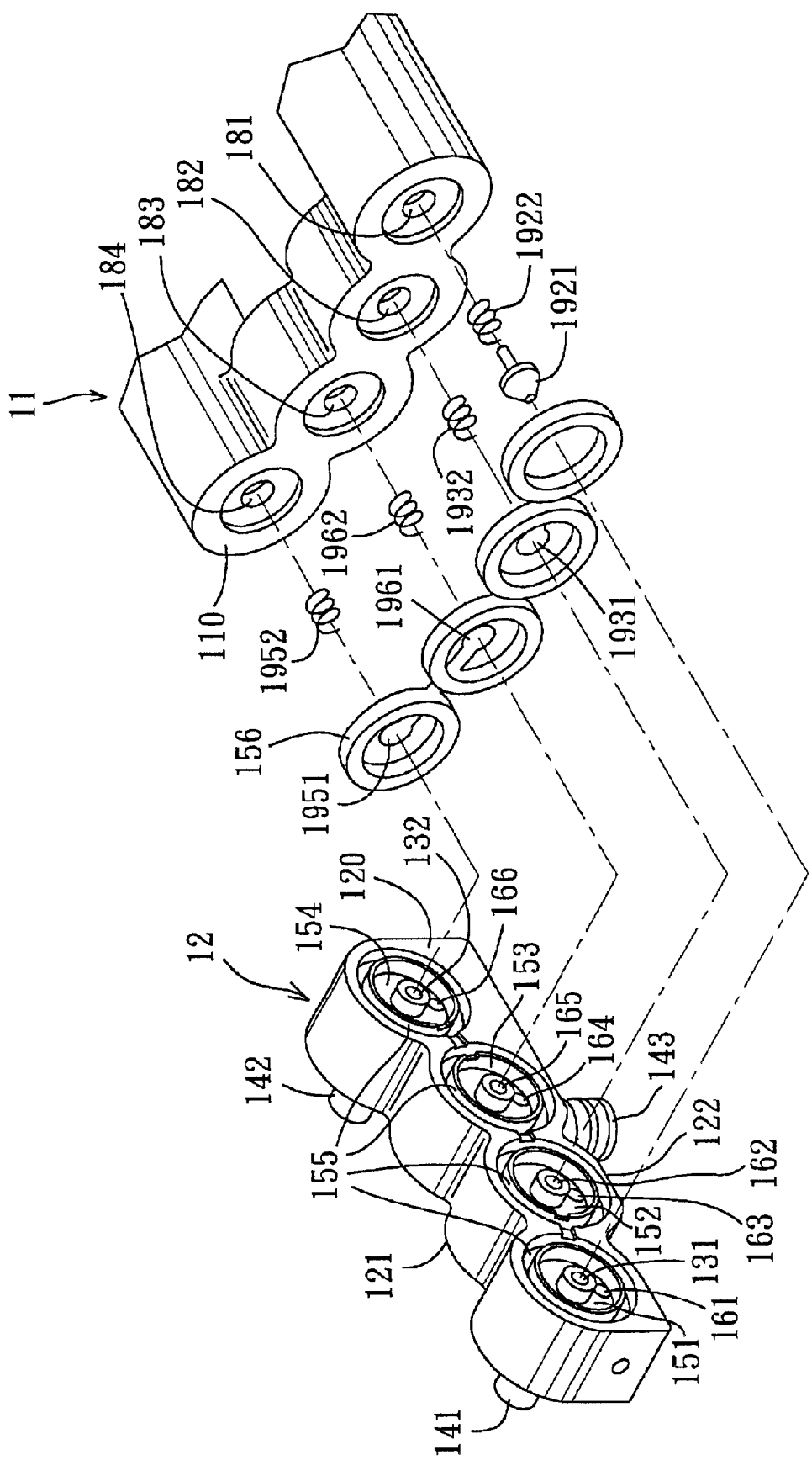
FIG. 2 is an exploded perspective view showing a water and air mixing mechanism of the preferred embodiment.
Figure 3:
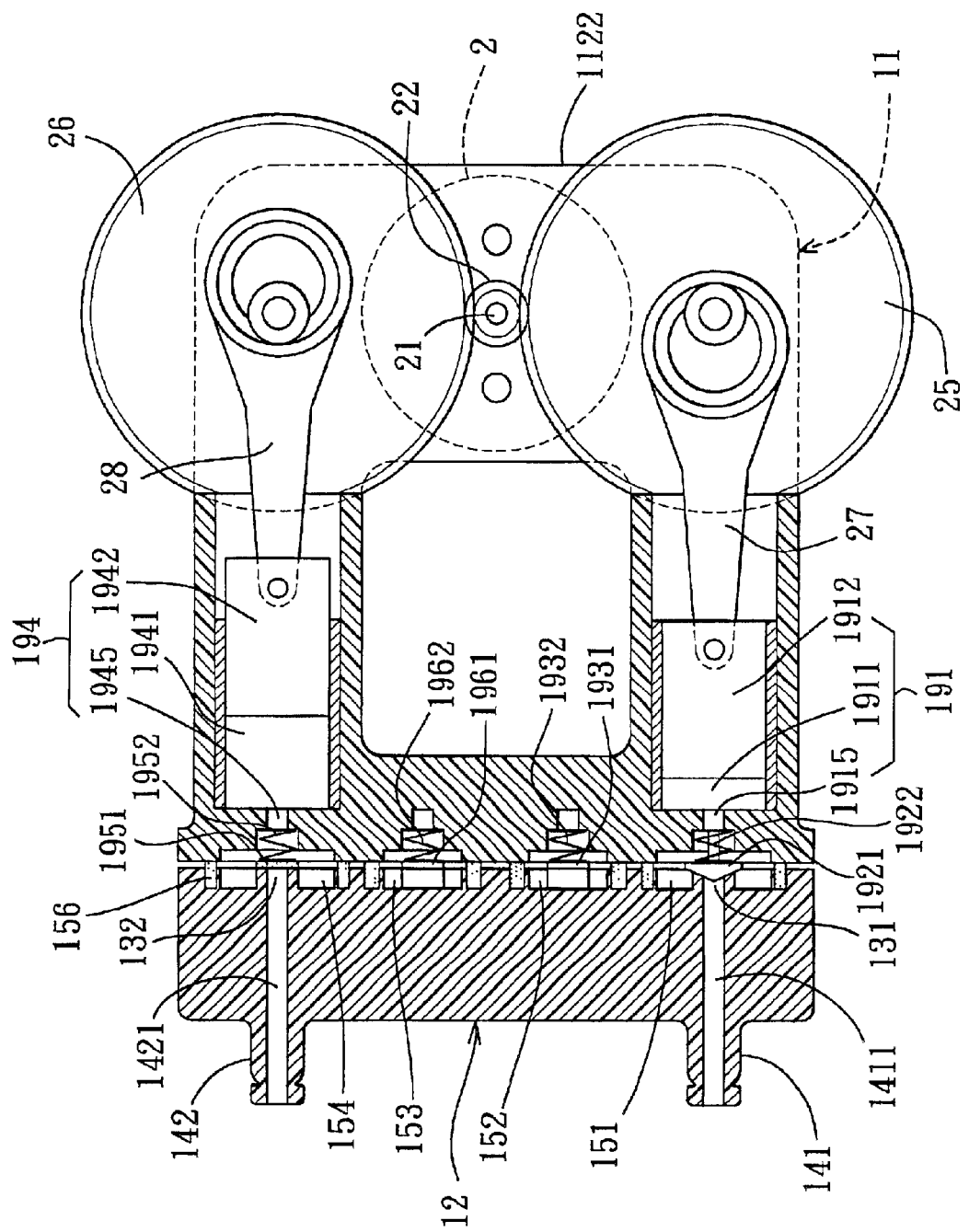
FIG. 3 is a sectional view showing the water and air mixing mechanism and a driving mechanism of the preferred embodiment.

Referring to FIGS. 1 to 3, the preferred embodiment of the device according to the present invention is shown to comprise a water and air mixing mechanism 1, a driving mechanism 2, and a mouthpiece 3.

The water and air mixing mechanism 1 includes front and rear mixing housings 12,11 coupled to each other in an axial direction at two coupling walls 120,110 thereof to form a water and air mixing body. On a front side 121 of the front mixing housing 12, a water inlet 141 is disposed to be connected to a tube 144 so as to receive a water flow from an outlet 145 of a reservoir, and an air inlet 142 is disposed to admit entrance of air stream.

Figure 4:
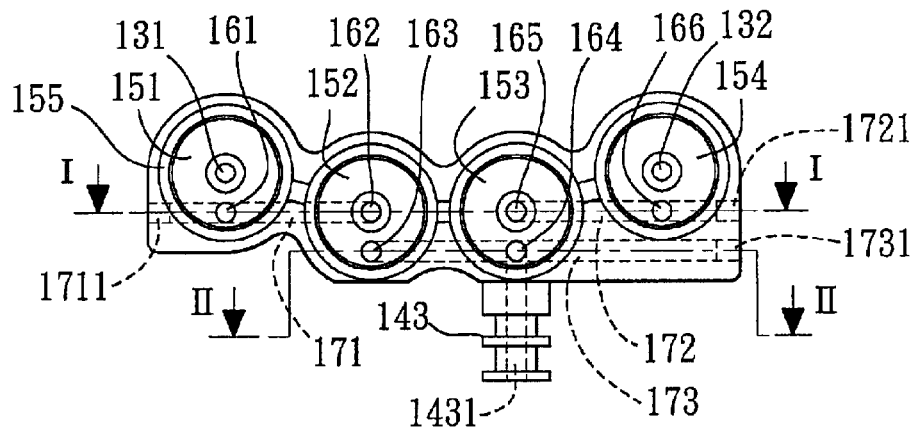
FIG. 4 is a front view showing a portion of the water and air mixing mechanism.
Figure 5:
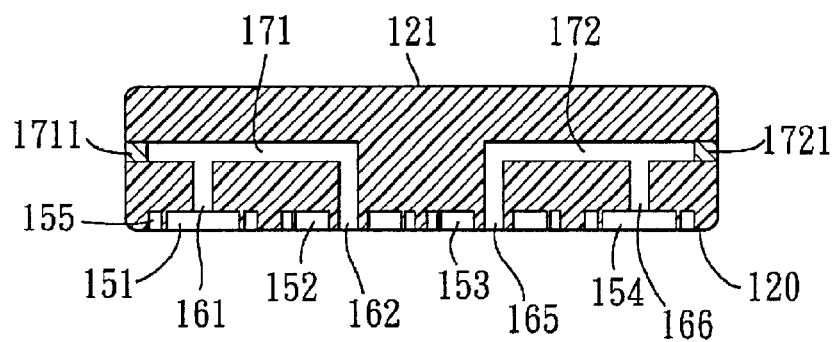
FIGS. 5 and 6 are partly cross-sectional views of the water and air mixing mechanism shown in FIG. 4, taken along lines I—I and II—II thereof, respectively.

With reference to FIGS. 4 and 5, the water and air mixing body defines first water and air transit chambers spaced apart from each other, and second water and air transit chambers spaced apart from each other. The first and second water transit chambers respectively have first water and air inlet ports 131,132 which are formed in the coupling wall 120 and which are communicated respectively with the water inlet 141 and the air inlet 142 via channels 1411,1421. In the coupling wall 120, two forwardly concaved portions 151, 154 are formed to surround respectively the first water and air inlet ports 131,132, and two forwardly concaved portions 152,153 are formed inboard to the concaved portions 151, 154. In addition, four through bores 161,166,163,164 are formed in the concaved portions 151,154,152,153, respectively. As shown in FIG. 5, first water and air outlet ports 171,172 are disposed to communicate with the through bores 161,166, and extend through the concaved portions 152,153, respectively. As such, the water flow and the air stream from the water and air inlets 141,142 pass respectively and sequentially through the first water and air inlet ports 131,132, the concaved portions 151,154, the through bores 161,166 and the first water and air outlet ports 171,172 which define the first water and air transit chambers.

Figure 6:
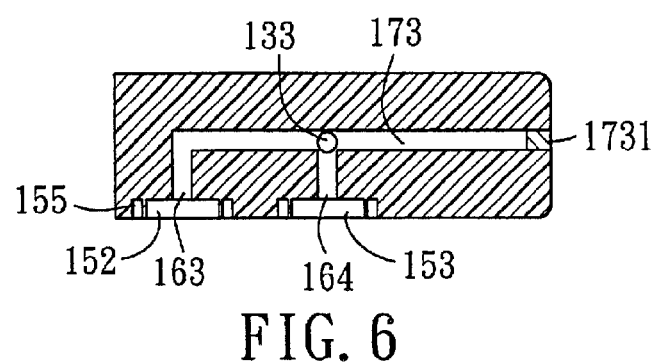

The second water and air transit chambers respectively have second water and air inlet ports 162,165 which are communicated respectively with the first water and air outlet ports 171,172 and which are disposed respectively adjacent to the through bores 163,164. Referring to FIGS. 4 and 6, the through bores 163,164 are formed respectively as second water and air outlet ports, and are communicated with a mixing port 133 via a channel 173. A mixing tube 143 is disposed on a bottom wall 122 of the mixing housing 12, and has a mixing outlet 1431 which is communicated with the mixing port 133 and which is connected to a flexible tube 146 for connection to the mouthpiece 3 (the construction thereof will be described below), as shown in FIG. 1. As such, the water flow and the air stream from the first water and air transit chambers can pass respectively and sequentially through the second water and air inlet ports 162,165, the concaved portions 152,153, the through bores 163,164, the channel 173, and are mixed in the mixing port 133 to generate air entrained water. The air entrained water flows sequentially into the mixing outlet 1431 and the flexible tube 146 so as to further spray out from the mouthpiece 3.

Preferably, referring to FIGS. 4 and 5, the through bore 161 and the second water inlet port 162 are flush with each other so as to facilitate forming of the first water outlet port 171 in a manner that the mixing housing 12 is drilled from a side thereof, and that a plug 1711 is used to close one end of the drilled hole. The first air outlet port 172 and the channel 173 are formed in the same manner, and are provided with plugs 1721,1731 to close one end of drilled holes thereof.

Moreover, referring again to FIG. 2, the coupling wall 110 of the rear mixing housing 11 is formed with four receiving through bores 181,182,183,184 that correspond with the concaved portions 151,152,153,154, respectively. The coupling wall 120 of the front mixing housing 12 is formed with four annular grooves 155 surrounding the concaved portions 151,152,153,154 such that four rubber O-ring seals 156 are received respectively therein.

Referring again to FIG. 3, first and second pumps 191,194 respectively have first and second internal ports 1915,1945 which are communicated respectively with the first water and air transit chambers in the axial direction via the receiving through bores 181,184 formed in the coupling wall 110 of the rear mixing housing 11 so as to be disposed respectively downstream of the first water and air inlet ports 131,132 and upstream of the first water and air outlet ports 171,172. Each of the first and second pumps 191,194 includes a cylinder 1911,1941 which is disposed in the rear mixing housing 11 and downstream of a respective one of the first and second internal ports 1915,1945, a piston 1912,1942 which is disposed in the cylinder 1911,1941 and which is movable reciprocally to sequentially pump in and out of a respective one of the first and second internal ports 1915,1945, the respective one of the water flow and the air stream, thereby accelerating the speeds of the water flow and the air stream so as to generate raised water and air pressures.

Referring to FIGS. 2 and 3, first and second valves 1921,1951 are disposed respectively between the first water inlet port 131 and the first internal port 1915, and between the first air inlet port 132 and the second internal port 1945. The first valve 1921 includes a valve portion which is disposed to be movable between first closed and open positions to respectively engage and disengage a valve seat portion of the first water inlet port 131, and a guiding rod which extends from the valve portion away from the valve seat portion and which is insertable into an inner annular wall of the receiving through bore 181 so as to guide movement of the valve portion. The second valve 1951 is a valve plate which is partially connected to the corresponding O-ring seal 156. Thus, when each of the first and second valves 1921,1951 is in the first closed position, a respective one of the water flow and the air stream, which is pumped out of a respective one of the first and second internal ports 1915,1945, is blocked from passing back through a respective one of the first water and air inlet ports 131,132, while proceeding further to flow through a respective one of the first water and air outlet ports 171,172. When each of the first and second valves 1921,1951 is in the first open position, the respective one of the water flow and the air stream is pumped in a respective one of the first water and air transit chambers as well as the respective one of the first and second internal ports 1915,1945 through the respective one of the first water and air inlet ports 131,132.

First and second biasing members 1922,1952 are coiled springs, each of which is disposed between the respective valve 1921,1951 and the respective receiving through bore 181,184 to move the valve 1921,1951 towards the first closed position.

Third and fourth valves 1931,1961 are valve plates which are partially connected to the corresponding O-ring seal 156. Each of the third and fourth valves 1931,1961 is moved by the respective one of the raised water and air pressures. Particularly, when a respective one of the first and second valves 1921,1951 is in the first open position, a respective one of the third and fourth valves 1931,1961 is in a second closed position, where the respective one of the water flow and the air stream, which has been pumped in the respective one of the first water and air transit chambers, is blocked from entering into a respective one of the second water and air outlet ports 163,164. Once the respective one of the first and second valves 1921,1951 is in the first closed position, the respective one of the third and fourth valves 1931,1961 will be in a second open position, where the respective one of the water flow and the air stream, which is flowing through the respective one of the first water and air outlet ports 171,172, further proceeds to the respective one of the second water and air outlet ports 163,164 through a respective one of the second water and air transit chambers.

Third and fourth biasing members 1932,1962 are coiled springs which are disposed between the respective valve 1931,1961 and the respective receiving through bore 182, 183 to bias the valves 1931,1961 to move towards the second closed position against the forces of the raised water and air pressure.

Referring to FIGS. 1 and 3, the driving mechanism 2 includes a motor with an output shaft 21 extending upwardly through a lower plate 1122 of a rear end 112 of the rear mixing housing 11, a driving gear 22 rotated by the output shaft 21, two transmission wheels 25,26 disposed between an upper plate 1121 of the rear end 112 and the lower plate 1122 to mesh with and to be driven by the driving gear 22 to rotate in opposite directions, and two piston rods 27, 28, each disposed to link the respective transmission wheel 25,26 and the piston 1912,1942 so as to transmit rotational force of the transmission wheel 25,26 to the piston 1912, 1942, thereby moving the piston 1912,1942 reciprocally in the corresponding cylinder 1911,1941. Furthermore, an electric wire 23 of the motor can be wound by a wire winding member 24 in a known manner.

The mouthpiece 3 includes a handle 31 communicated with the flexible tube 146, a nozzle 32 with a plurality of spray holes 321, and a control valve 311 to control the amount of water sprayed from the spray holes 321. The flexible tube 146 can be wound by a tube winding member 33.

With such a construction, the first and second pumps 191,194 are driven by the driving mechanism 2 to pump the water flow when pumping the air stream out, and to pump the water flow out when pumping the air stream in. Therefore, the water flow and the air stream with constant amounts can flow alternately into the mixing outlet 1431, thereby resulting in a good cleaning effect and a comfortable feeling for the user.

Figure 7:
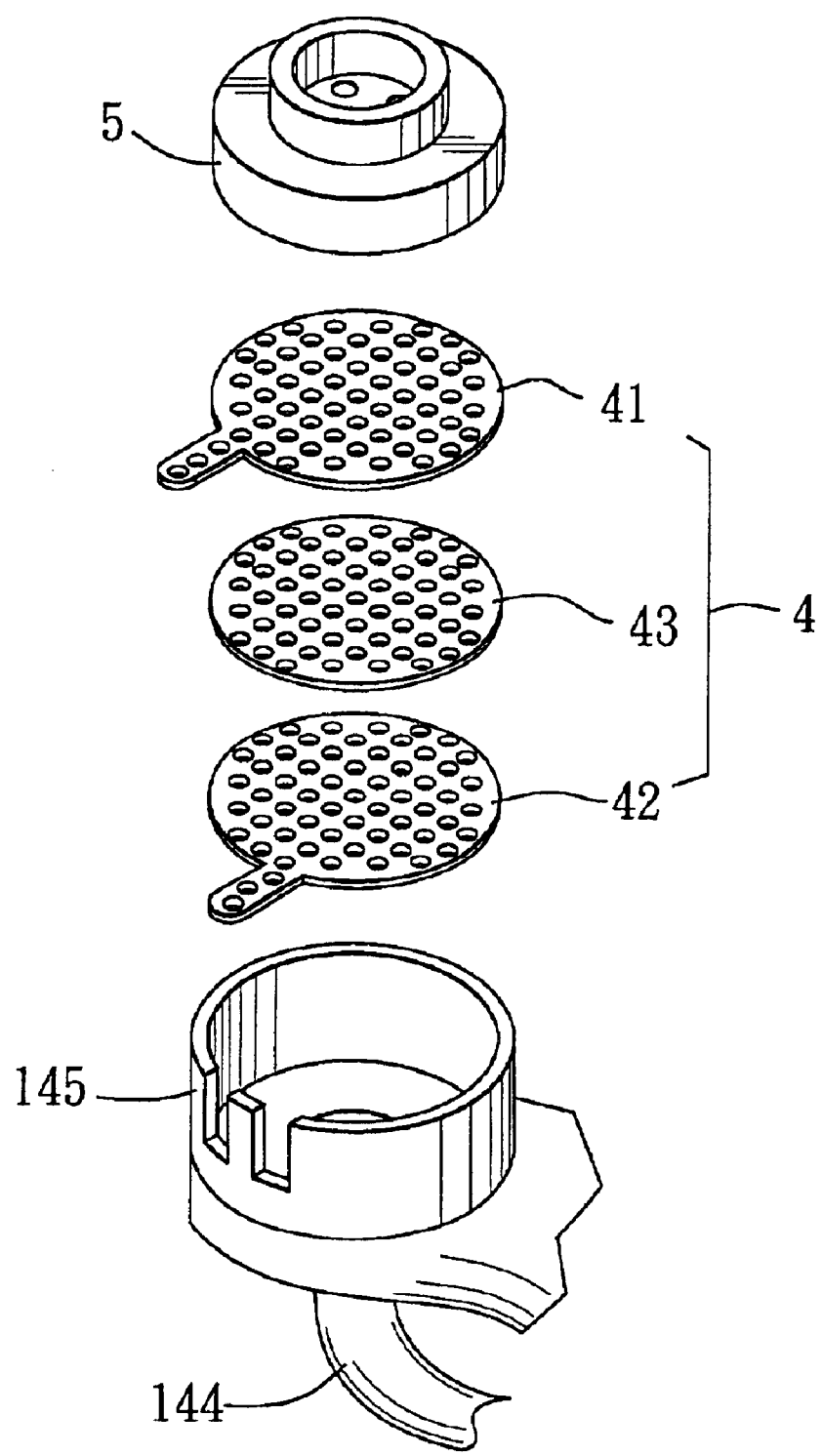
FIG. 7 is an exploded perspective view of an ion-generating member of the preferred embodiment.

Preferably, referring to FIGS. 1 and 7, an ion-generating member 4 is disposed to communicate with and upstream of a connecting head 145 of the tube 144, and includes porous positive, negative, and intermediate plates 41,42,43 to convert water of the water flow into ion-enriched water in a known manner so as to enhance the teeth cleaning effect. A cap 5 covers the connecting head 145 and communicates with the reservoir.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

We claim:

1. A device for generating a jet stream of air entrained water, comprising:

a water inlet adapted to receive a water flow from a reservoir;

an air inlet adapted to admit entrance of air stream;

a water and air mixing body defining:

first water and air transit chambers spaced apart from each other, and respectively having first water and air inlet ports which are disposed to be communicated respectively with said water inlet and said air inlet, and first water and air outlet ports which are disposed respectively downstream of said first water and air inlet ports, and second water and air transit chambers spaced apart from each other, and respectively having second water and air inlet ports which are disposed to be communicated respectively with said first water and air outlet ports, and second water and air outlet ports which are disposed respectively downstream of said second water and air inlet ports;

first and second pumps respectively having first and second internal ports which are communicated respectively with said first water and air transit chambers, and which are disposed respectively downstream of said first water and air inlet ports and upstream of said first water and air outlet ports, said first and second pumps being configured to sequentially pump in and out of said first and second internal ports respectively, the water flow and the air stream respectively, thereby accelerating the speeds of the water flow and the air stream respectively so as to generate raised water and air pressures, respectively;

first and second valves disposed respectively between said first water inlet port and said first internal port, and between said first air inlet port and said second internal port, each of said first and second valves being further disposed to be movable between a first closed position, where a respective one of the water flow and the air stream, being pumped out of a respective one of said first and second internal ports, is blocked from passing through a respective one of said first water and air inlet ports, while proceeding further to flow through a respective one of said first water and air outlet ports, and a first open position, where the respective one of the water flow and the air stream is pumped in a respective one of said first water and air transit chambers as well as the respective one of said first and second internal ports through the respective one of said first water and air inlet ports;

third and fourth valves disposed respectively between said second water inlet port and said second water outlet port, and between said second air inlet port and said second air outlet port, each of said third and fourth valves being further disposed to be moved by the respective one of the raised water and air pressures from a second closed position, where the respective one of the water flow and the air stream, which is being pumped in the respective one of said first water and air transit chambers when the respective one of said first and second valves is in the first open position, is blocked from entering into a respective one of said second water and air outlet ports, to a second open position, where the respective one of the water flow and the air stream, which is flowing through the respective one of said first water and air outlet ports when the respective one of said first and second valves is in the first closed position, further proceeds to the respective one of said second water and air outlet ports through a respective one of said second water and air transit chambers; and a mixing outlet disposed downstream of and disposed to merge said second water and air outlet ports so as to obtain an accelerated stream of the air entrained water.

2. The device of claim 1, further comprising:

first and second biasing members disposed to bias respectively said first and second valves to move towards the first closed position; and third and fourth biasing members disposed to bias respectively said third and fourth valves to move towards the second closed position against the forces of the raised water and air pressure.

3. The device of claim 2, wherein said first water inlet port is spaced apart from said first internal port in an axial direction, said first water inlet port having a valve seat portion formed therein, said first internal port having an inner annular wall formed therein and extending in the axial direction to define a receiving through bore, said first valve including a valve portion which is disposed to engage or disengage said valve seat portion in the first closed or open positions respectively, and a guiding rod which extends from said valve seat portion away from said valve seat portion and which is insertable into said receiving through bore so as to guide movement of said valve portion to engage or disengage said valve seat portion, said first biasing member being a coiled spring which is disposed between said valve portion and said inner annular wall to move said valve portion towards the first closed position.

4. The device of claim 3, wherein each of said second, third and fourth valves is a check valve.

5. The device of claim 2, further comprising a driving mechanism disposed to drive said first pump to pump the water flow in when driving said second pump to pump the air stream out, and to drive said first pump to pump the water flow out when driving said second pump to pump the air stream in.

6. The device of claim 5, wherein each of said first and second pumps includes
   a cylinder disposed downstream of a respective one of said first and second internal ports and upstream of said first and second water and air outlet ports, and
   a piston disposed in said cylinder and movable reciprocally to pump the respective one of the water flow and the air stream in and out of said first and second internal ports.

7. The device of claim 6, wherein said driving mechanism includes
   a motor with an output shaft,
   a driving gear rotated by said output shaft,
   two transmission wheels disposed to mesh with and to be driven by said driving gear to rotate in opposite directions, and
   two piston rods, each disposed to link a respective one of said transmission wheels and said piston so as to transmit rotational force of the respective one of said transmission wheels to said piston, thereby moving said piston reciprocally in said cylinder.

8. The device of claim 2, further comprising an ion-generating member disposed upstream of said water inlet to convert water of the water flow into ion-enriched water.

9. The device of claim 2, further comprising a mouthpiece coupled to said mixing outlet to spray the accelerated stream of the air entrained water.

\* \* \* \* \*